(12) United States Patent
Wu (10) Patent No.: US 7,261,685 B2
(45) Date of Patent: Aug. 28, 2007

(54) ON-GENITAL ERECTION DEVICE AND SYSTEM FOR COITAL USE

(76) Inventor: Chang Jy Richard Wu, 19907 Tennessee Trail, Walnut, CA (US) 91789

( * ) Notice: Subject to any disclaimer, the term of this patent is extended or adjusted under 35 U.S.C. 154(b) by 0 days.

(21) Appl. No.: 11/103,908

(22) Filed: Apr. 12, 2005

(65) Prior Publication Data

US 2006/0229494 A1 Oct. 12, 2006

(51) Int. Cl.
*A61F 5/00* (2006.01)

(52) U.S. Cl. ........................................................ 600/39

(58) Field of Classification Search ................ 128/844, 128/897, 898; 600/38–41
See application file for complete search history.

(56) References Cited

U.S. PATENT DOCUMENTS 4,175,554 A * 11/1979 Gerow ........................ 600/38
5,894,615 A * 4/1999 Alexander ................... 5/421
6,569,083 B1 * 5/2003 Kassman ..................... 600/38
2004/0031491 A1 * 2/2004 Praml ........................ 128/844

* cited by examiner

Primary Examiner—Samuel G. Gilbert
(74) Attorney, Agent, or Firm—Chein-Hwa S Tsao (57) ABSTRACT

An on-genital erection device for inducing and maintaining the human sexuality are proposed. The on-genital erection device includes an essentially cylindrical elastomeric sleeve surrounding the pre-erection penis. The elastomeric sleeve includes self-sealing air-ports for engaging with an air pump thus forming an expandable and suctioning air tight enclosure of the penis causing its erection. The elastomeric wall can be made of a laminate of at least two layers $L_i$, i=1, 2, . . . , M. Each $L_i$ includes a surface relief pattern forming a surface relief pattern set that in turn defines a plurality of air paths $PT_j$ wherein at least one air path $PT_k$ is communicatively connected with the penis surface. Thus, after the plurality of air paths $PT_j$ get engaged through their respective air-ports with an external multi-port air pumping device, the desired expandable and suctioning enclosure is formed.

12 Claims, 9 Drawing Sheets

ON-GENITAL ERECTION DEVICE AND SYSTEM FOR COITAL USE

CROSS REFERENCE TO RELATED APPLICATION

BACKGROUND OF THE INVENTION

1. Field of the Invention

The present invention relates generally to the field of entertainment devices. More particularity, the present invention is directed to an entertainment device and associated system for the inducement and pleasure enhancement of human sexuality.

2. Description of the Related Art

Many entertainment devices have long existed for the inducement and pleasure enhancement of human sexuality. One class of devices for inducing and enhancing the human sexuality are numerous ingestive drugs, generally called aphrodisiacs, for chemically causing a human sexual biological arousal during a following time period hence a corresponding genital erection for coitus. An example is the popular erectile dysfunction therapeutical drug Viagra™, also known under the generic name sildenafil citrate, produced by the Pfizer Inc. While easy to use and clinically proven effective, these ingestive drugs in many cases can cause undesirable side effects and the associated health risk can be especially troublesome if they were of a long termed nature. Another class of devices for the same purpose are pure physical devices directed at physically stimulating the human genitals without any ingestive chemicals hence more preferable from the perspective of fewer side effects. However, ease of use can be an issue here. As an example, a vacuum suction device in the form of a hand-pumped bell jar has been used for many years. The bell jar has a tapered tubular rubber mouth piece for insertion of a pre-erection penis. The bell jar interior is then hand-pumped to a negative pressure $-\Delta P$ below the ambient causing a partial vacuum therein thus forcefully suctioning the inserted penis to full expansion and erection before a following coitus. However, the now fully expanded and erected penis tends to get stuck in the now undersized mouth piece and becomes awkward to remove there from hence causing a distracting anxiety. Furthermore, even if the removal of the erected penis can be made easy, no longer will there be a guaranteed maintenance of erection during a following coitus activity hence potentially resulting in a still unsatisfactory performance. This can be especially troublesome for those biologically lack of power to maintain a full erection throughout the coitus. Therefore, for the class of pure physical devices, there has been a need of ease of use plus the capability of maintaining full erection throughout and possibly even after coitus considering the generally different time-response curves between male and female.

SUMMARY OF THE INVENTION

An easy-to-use on-genital erection device and system for inducing and maintaining the human sexuality are proposed. Under an X-Y-Z coordinate system with the direction of an erected penis designated as Z-direction and the penis base plane designated as X-Y plane, the on-genital erection device includes a cylindrical elastomeric sleeve surrounding the pre-erection penis upon placing the sleeve base at the penis base. The elastomeric sleeve includes through-wall self-sealing air-ports for functionally engaging with an external air pumping device thus forming an expandable and suctioning air tight enclosure of the penis surface hence causing an expansion and erection of the penis.

The elastomeric sleeve further includes a ring surrounding the penis base. This ring is undersized relative to the fully-expanded penis base diameter thus forming an extra air tight seal against a back blood flow out of the penis hence prolonging the penis erection during and after subsequent coitus.

The front end rim of the elastomeric sleeve near the penis glans is shaped to facilitate a manual seal by the user to accelerate an early-stage expansion and erection of the penis.

The elastomeric sleeve further includes at least one activable through-wall air-releasing devices for, upon user activation, causing a collapse of the air tight enclosure hence facilitating its removal from the penis after use.

In one embodiment, the cylindrical diameter of the elastomeric sleeve is set to be about the same as the post-erection penis shaft diameter and the Z-direction length of the fully expanded elastomeric sleeve is set to be about the same as the post-erection penis shaft length.

In another embodiment, the front end rim of the elastomeric sleeve near the penis glans and/or the rear end rim of the elastomeric sleeve near the penis base can be coated with a biologically inert sealant to form an extra air tight rim seal against physical movements during subsequent coitus.

The front end of the elastomeric sleeve near the penis glans can be further closed off with a cap structure to form an air tight glans enclosure and to simultaneously act as a biological barrier hence performing a condom function.

In another embodiment, the elastomeric sleeve includes a serially joined aft section located at the penis base, a middle section located near the middle of the penis shaft and a fore section located near the penis glans with the middle section having a cylindrical diameter about the same as the post-erection penis shaft diameter while having a Z-direction length less than the post-erection penis shaft length, the aft section in the form of a truncated cone pointing in the negative Z-direction and having a base diameter about the same as and circumferentially joined with the middle section while having a top diameter less than the post-erection penis shaft diameter, and the fore section in the form of a truncated cone pointing in the Z-direction and having a base diameter about the same as and circumferentially joined with the middle section while having a top diameter less than the post-erection penis shaft diameter.

In another embodiment, at least a portion of the elastomeric sleeve has the form of a linear bellows extensible along the Z-direction for forming an expandable and suctioning air tight enclosure covering essentially the entire post-erection penis shaft length.

In another embodiment, at least a portion of the elastomeric sleeve has the form of an angular bellows expandable along the radial-direction for forming an expandable and suctioning air tight enclosure accommodating essentially the post-erection penis shaft diameter.

In another embodiment, the wall of the elastomeric sleeve can be made of a laminate of at least two layers $L_i$, i=1, 2, ..., M and M>=2. Each $L_i$ further includes a surface relief pattern $RP_i$ such that the corresponding surface relief pattern set $RP_{SET}$, $(RP_1, RP_2, \ldots, RP_M)$, jointly define a plurality of air paths $PT_j$ and respectively connected externally engageable self-sealing air-ports $AP_j$, j=1, 2, ..., N and N>=2. Furthermore, all members of an air path subset $PT_{sub}$ with at least one air path $PT_j$ are communicatively connected with the penis surface. Thus, after the air path subset $PT_{sub}$ get functionally engaged through the air-ports $AP_j$ with an external multi-port air pumping device, the desired expandable and suctioning air tight enclosure is formed.

In another embodiment, the surface relief pattern set $RP_{SET}$ of the above are patterned such that at least a portion of the surface of the air path subset $PT_{sub}$ in contact with the penis surface further includes a plurality of concave scallops causing the build-up of a plurality of matching convex surface scallops from the so-contacted penis surface thus forming an extra air tight seal against physical movements during subsequent coitus.

In another embodiment, the surface relief pattern set $RP_{SET}$ of the above are patterned such that the surface of the air path subset $PT_{sub}$ in contact with the penis surface further includes a plurality of one-way valves allowing the formation of the expandable and suctioning air tight enclosure while blocking a loss of suctioning power during subsequent coitus.

In another embodiment, one or more members of the remaining air paths $PT_k$, other than those of the air path subset $PT_{sub}$, can be functionally engaged through a corresponding air-port $AP_k$ with the external multi-port air pumping device and evacuated to a negative pressure relative to the ambient, $-\Delta P_k$. An extra air tight seal is thus formed at a penis surface area surrounded by $PT_k$ against physical movements during subsequent coitus.

Specifically, the selected member of the remaining air paths $PT_k$ from the above can be an annular ring surrounding the penis base. An extra air tight seal against a back blood flow out of the penis is thus formed hence prolonging the penis erection during and after subsequent coitus.

In another embodiment, one or more members of the remaining air paths $PT_k$, other than those of the air path subset $PT_{sub}$, can be functionally engaged through a corresponding air-port $AP_k$ with the external multi-port air pumping device and pressurized to a positive pressure relative to the ambient, $+\Delta P_k$, thus hardening and rigidizing a penis surface area surrounded by $PT_k$ for subsequent coitus.

In another embodiment, one or more members of the remaining air paths $PT_k$ surrounding the penis shaft, other than those of the air path subset $PT_{sub}$, can be functionally engaged through a corresponding air-port $AP_k$ with the external multi-port air pumping device and pressurized to a positive pressure relative to the ambient, $+\Delta P_k$, thus increasing the apparent thickness of the penis shaft for subsequent coitus.

In a refinement, the above positive pressure $+\Delta P_k$ can be made time-varying thus causing a corresponding vibration of the apparently increased thickness of the penis shaft.

In another embodiment, one or more members of the remaining air paths $PT_k$ surrounding the penis shaft, other than those of the air path subset $PT_{sub}$, can be functionally engaged through a corresponding air-port $AP_k$ with the external multi-port air pumping device and pressurized to a positive pressure relative to the ambient, $+\Delta P_k$, to create a number of protuberances along the penis surface for subsequent coitus.

In a refinement, the above positive pressure $+\Delta P_k$ can be made time-varying thus causing a corresponding vibration of the created protuberances along the penis surface.

In another embodiment, one or more layers $L_i$ can be made of a piezoelectric material and covered with a number of opposing electrode pairs. Upon their connection to an external Alternating Current (AC) electrical signal source, the piezoelectric material can also cause a corresponding penis vibration.

In another embodiment, one or more layers $L_i$ can be coated with a resistive heating material terminated with a number of input electrodes. Upon their connection to an electrical power source, the resistive heating material can cause a corresponding warming of the penis.

In yet another embodiment, one member of the remaining air paths $PT_k$, other than those of the air path subset $PT_{sub}$, is a strut with the following constituents:
 a) an annular base ring surrounding the penis base.
 b) a plurality of Z-direction columns, distributed around the periphery of the penis shaft, respectively connected to the annular base ring.
 c) an annular glans ring, surrounding the penis glans, connected to the glans end of the Z-direction columns.

To the accomplishment of the above and related objects, this invention may be embodied in the form illustrated in the accompanying drawings, attention being called to the fact, however, that the drawings are illustrative only, and that changes may be made in the specific construction illustrated.

BRIEF DESCRIPTION OF THE DRAWINGS

Various other objects, features and attendant advantages of the present invention will become fully appreciated as the same becomes better understood when considered in conjunction with the accompanying drawing, in which like reference characters designate the same or similar parts throughout the several views, and wherein.

DETAILED DESCRIPTION OF THE PREFERRED EMBODIMENTS

In the following detailed description of the present invention, numerous specific details are set forth in order to provide a thorough understanding of the present invention. However, it will become obvious to those skilled in the art that the present invention may be practiced without these specific details. In other instances, well-known methods, procedures, materials and components have not been described in detail to avoid unnecessary obscuring aspects of the present invention. The detailed description is presented largely in terms of simplified perspective views, sectional views and block diagrams. These descriptions and representations are the means used by those experienced or skilled in the art to concisely and most effectively convey the substance of their work to others skilled in the art.

Reference herein to "one embodiment" or an "embodiment" means that a particular feature, structure, or characteristics described in connection with the embodiment can be included in at least one embodiment of the invention. The appearances of the phrase "in one embodiment" in various places in the specification are not necessarily all referring to the same embodiment, nor are separate or alternative embodiments mutually exclusive of other embodiments. Further, the order of process flow representing one or more embodiments of the invention do not inherently indicate any particular order nor imply any limitations of the invention.

Figure 1A:
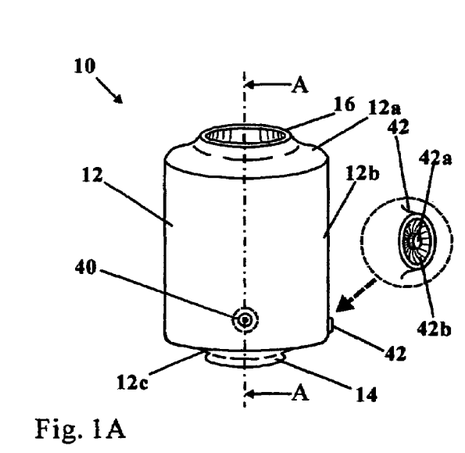
FIG. 1A and FIG. 1B are perspective and sectional views of an embodiment of the present invention on-genital erection device.
Figure 1B:
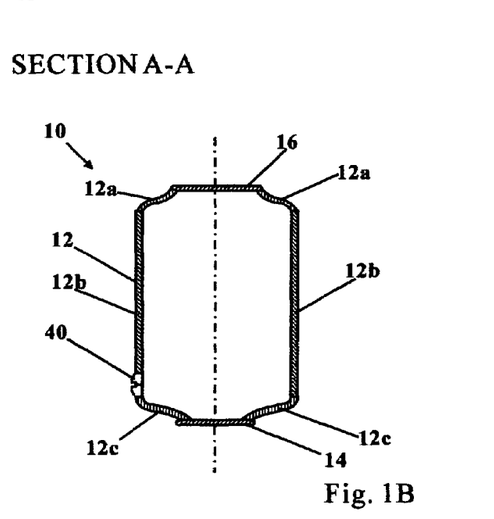

FIG. 1A and FIG. 1B are perspective and sectional views of an embodiment of the present invention on-genital erection device 10 for the preparation for and use in coitus. For convenience, an X-Y-Z Cartesian coordinate system is adopted and shown with the direction of an erected penis designated as Z-direction and the penis base plane designated as X-Y plane. FIG. 2A, FIG. 2B, FIG. 2C and FIG. 2D together illustrate an application sequence of the on-genital erection device 10. The on-genital erection device 10 is a substantially cylindrical elastomeric sleeve 12 surrounding a pre-erection penis 420 upon placement of the sleeve base 14, here in the form of a rim, for a snug fit at a user's penis base 400. There are a through-wall air-port 40 and an air-releasing device 42 located on the wall of the on-genital erection device 10 near its sleeve base 14. The air-releasing device 42 can be activated by a user to cause a rapid air exchange hence pressure balance between the interior of the elastomeric sleeve 12 and the ambient. In one embodiment as illustrated in an enlarged inset at the right side of FIG. 1A, the user-activable through-wall air-releasing device 42 includes a push button 42a located at the bottom of a surface recess 42b so as to avoid an unintentional activation by the user. For those skilled in the art numerous ways exist to implement the air-releasing device 42. For example, a matched pair of axially-tapered spring-loaded plunger and through-wall bore will do. More on the application scenario of the air-releasing device 42 will be presently described.

Figure 2A:
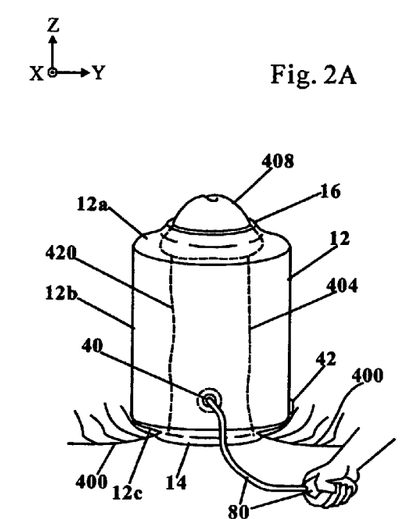
FIG. 2A, FIG. 2B, FIG. 2C and FIG. 2D together illustrate an application sequence of the embodiment from FIG. 1A and FIG. 1B.
Figure 2B:
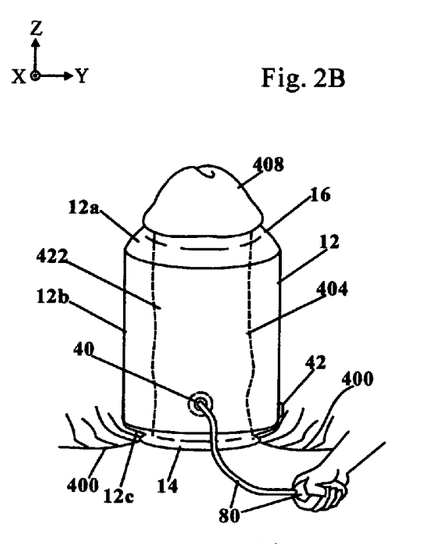
Figure 2C:
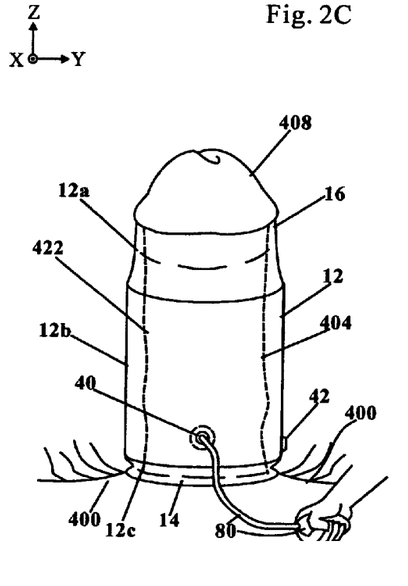

The wall structure of the elastomeric sleeve 12 includes three serially joined sections. Upon placement of the on-genital erection device 10 onto and surrounding a pre-erection penis 420 as illustrated in FIG. 2A, the three sections are an aft section 12c located at the penis base 400, a middle section 12b located near the middle of the penis shaft 404 and a fore section 12a located near the penis glans 408. As more clearly illustrated in FIG. 1B that is a sectional view along section A-A of FIG. 1A, the cylindrical diameter of the middle section 12b is about the same as the shaft diameter of the post-erection penis 424 while the Z-direction length of the middle section 12b is made less than the shaft length of the post-erection penis 424. The aft section 12c is shaped in the form of an expandable truncated cone pointing in the negative Z-direction. Its base diameter is about the same as and circumferentially joined with the middle section 12b. The top diameter of the aft section 12c is made less than the shaft diameter of the post-erection penis 424. The fore section 12a is also shaped in the form of an expandable truncated cone pointing in the Z-direction and topped with a front end rim 16. The base diameter of the fore section 12a is about the same as and circumferentially joined with the middle section 12b. The top diameter of the front end rim 16 is made less than the shaft diameter of the post-erection penis 424 while only slightly less than the diameter of penis glans 408 of a pre-erection penis 420. Therefore for those cases where the pre-erection penis 420 is long enough that the tip of penis glans 408 sticks through the front end rim 16, as illustrated in FIG. 2A, the front end rim 16 together with the penis glans 408 forms an automatic sealing of the elastomeric sleeve 12. However, while not shown here, for cases where the pre-erection penis 420 is too short for the tip of penis glans 408 to stick through the front end rim 16, the user can still effect a manual seal of the elastomeric sleeve 12 by pressing down on the front end rim 16.

Figure 2D:
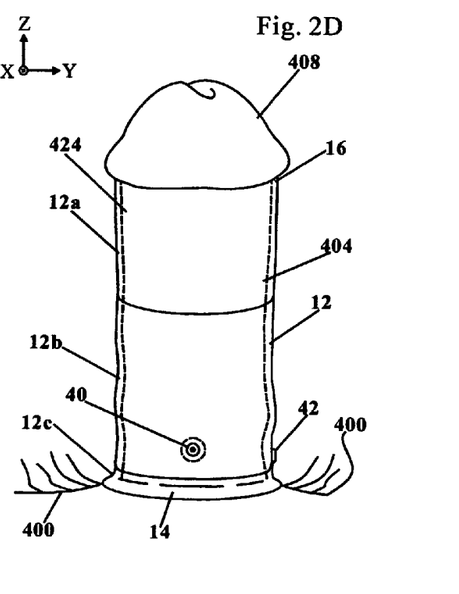

In any case, after the air-port 40 gets functionally engaged with an external hand air pump 80 designed for a vacuum mode as illustrated in FIG. 2A, an action of air suction from the external hand air pump 80 gets ported through the air-port 40 and acts upon the pre-erection penis 420 at the interior of the elastomeric sleeve 12. Therefore, upon subsequent vacuum pumping with the external hand air pump 80 as illustrated from FIG. 2B to FIG. 2D, the pre-erection penis 420 goes through a significant expansion and erection stages of erecting penis 422 and post-erection penis 424. This is caused by a vacuum suction induced arterial blood inflow to the three cylinders of spongy tissue, a lower cylinder called corpus spongiosum and two upper cylinders called corpora cavernosa each. Notice that, due to the initial geometry of the elastomeric sleeve 12 of FIG. 2A, the pre-erection penis 420 initially only primarily expands in a radial direction perpendicular to the Z-direction. However, upon further radial expansion of the erecting penis 422, due to blood spreading within the three spongy cylinders a concomitant Z-direction extension of the penis also takes place. The same mechanism also causes a significant expansion of the penis glans 408 further strengthening the sealing of the front end rim 16 against physical movements during subsequent coitus. Notwithstanding the presence of this mechanism, a preferred embodiment is to make the Z-direction length of the middle section 12b at least about 50% of the post-erection penis 424 shaft length for a rapid and efficient erection process. Similarly, it is also preferable to set the Z-direction length of the fully expanded elastomeric sleeve 12 to be about the same as the shaft length of the post-erection penis 424 and the cylindrical diameter of the elastomeric sleeve 12 to be about the same as the shaft diameter of the post-erection penis 424. An additional embodiment is to have the front end rim 16 or the sleeve base 14 coated with a biologically inert sealant, such as a mineral grease or Vaseline™, a petroleum jelly, to form an extra air tight and persistent rim seal against physical movements during subsequent coitus. Yet another important aspect of the present invention is that the continuing then fully-expanded penis base diameter of the post-erection penis 424 has now become significantly oversized with respect to the used to be snug-fit sleeve base 14. The resulting significant stretching of the sleeve base 14 in turn forms an extra air tight seal against a veinal blood outflow from the post-erection penis 424 hence prolonging the penis erection during and even after a subsequent ejaculation. This mechanism can effect a closer matching of the male-female temporal sexual responses. To accommodate an anticipated wide variation of penis sizes amongst the user population, the elastomeric sleeve 12 can be made with more than one sizes. As a safety measure against a prolonged erection of the post-erection penis 424, the air-releasing device 42 can be activated by the user anytime to effect a pressure balance between the interior of the elastomeric sleeve 12 and the ambient, collapsing the elastomeric sleeve 12 from the penis surface, followed by an easy removal of the on-genital erection device 10 from the penis. While the location of the air-port 40 and the air-releasing device 42 can be anywhere along the penis shaft 404 preferably they should be located near the penis base 400 to reduce a corresponding mechanical interference with the following coitus activity. To avoid air leakage where the external hand air pump 80 is disengaged following full erection, as illustrated in FIG. 2D, the air-port 40 should be designed as self-sealing, similar to that of a basketball, hence maintaining, after its disengagement from the external hand air pump 80, an active suctioning hence erection of the post-erection penis 424 for coitus. It is further noted that, while the post-erection penis 424 is shown disengaged from the external hand air pump 80 before coitus, the external hand air pump 80 does not have to be disengaged especially if the external hand air pump 80 is made compact in size and properly tucked away from interfering with the coitus. There are many material choices for the elastomeric sleeve 12. Some examples are natural rubber, synthetic rubber such as latex rubber and polyurethane rubber.

Figure 3A:
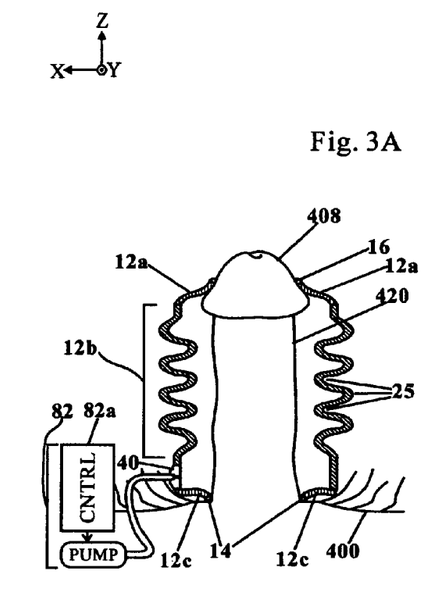
FIG. 3A, FIG. 3B, FIG. 3C and FIG. 3D together illustrate the application sequence of additional embodiments of linear bellows and cap structure.
Figure 3B:
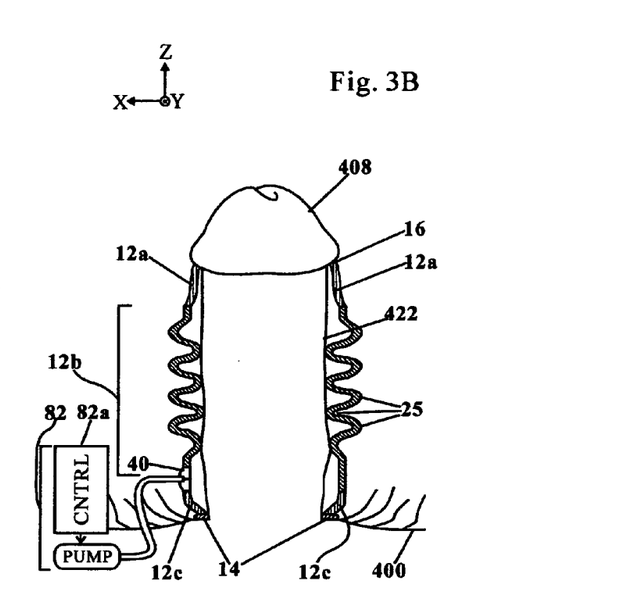
Figure 3C:
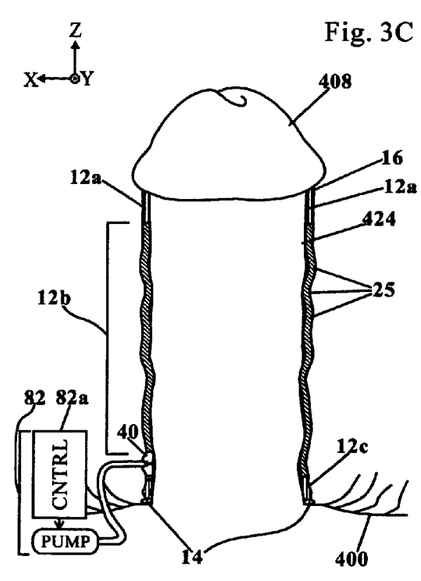
Figure 3D:
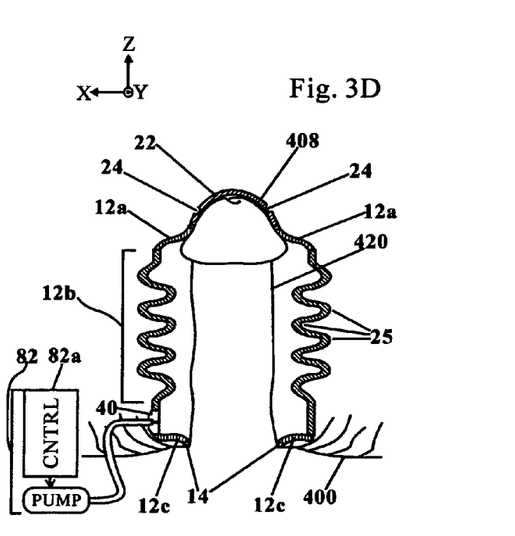

FIG. 3A, FIG. 3B, FIG. 3C and FIG. 3D together illustrate the application sequence of additional embodiments of linear bellows and cap structure. The embodiment of FIG. 3A is the same as FIG. 2A except that the structure of the middle section 12b is a linear bellows 25. As illustrated with the graphical sequence from FIG. 3A to FIG. 3C, the linear bellows 25 are extensible along the Z-direction making the fully expanded elastomeric sleeve 12 covering essentially the entire post-erection penis 424 shaft length. Of course, other parts of the elastomeric sleeve 12 can have a structure similar to the linear bellows 25 as well, such as the fore section 12a or the aft section 12c. Notice that, instead of a hand air pump, an external electrical air pump 82 is used here to engage the air-port 40. The external electrical air pump 82 can be implemented with varieties such as a piston-type pump, a bellows pump, a gear pump, a van pump or a peristaltic pump. The external electrical air pump 82 further includes an electronic control 82a for an increased accuracy and flexibility of its pumping power. For example, pressure sensors and feedback controls can be introduced into the control 82a to reach a self-terminating pre-determined pressure $-\Delta P_k$ below the ambient. For another example, the pumping power can be made time-varying to achieve additional functionality and this will be presently described. The embodiment of FIG. 3D is the same as FIG. 3A except that the front end of the elastomeric sleeve 12 near the penis glans 408 is now closed off with an added cap structure 22. The junction between the added cap structure 22 and the fore section 12a is further weakened with a user-breakable indentation 24. Functionally, the cap structure 22 forms an air tight enclosure next to the penis glans 408 thus accelerates the corresponding expansion and erection of the pre-erection penis 420. While not specifically illustrated here, the cap structure 22 is to be broken off the on-genital erection device 10 along the indentation 24 after achieving full erection. Thereafter, the penis glans 408 is fully exposed for an improved sensitivity during following coitus. Alternatively, the indentation 24 can even be made automatically breakable by the advancing and expanding penis glans 408 during the penis erection process. Of course, the indentation 24 can alternatively be any other surface-weakening mechanical feature such as an emboss. Yet another embodiment is to eliminate the indentation 24 all together. In this case the cap structure 22 gets to stay on the on-genital erection device 10 thus forming a biological barrier of the post-erection penis 424 like a regular condom during following coitus.

Figure 4A:
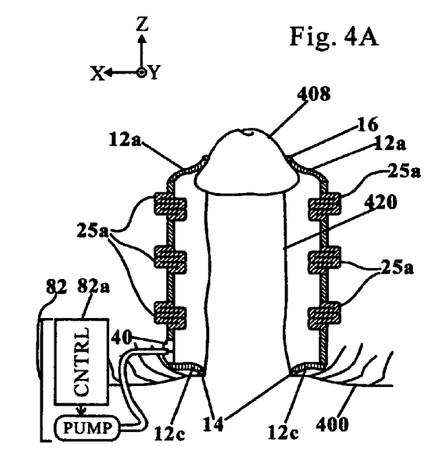
FIG. 4A and FIG. 4B together illustrate the application sequence of another embodiment of linear bellows with consecutively packed folds.
Figure 4B:
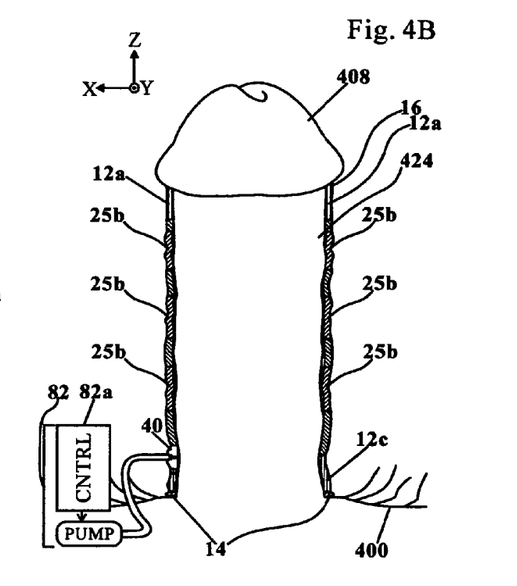

FIG. 4A and FIG. 4B together illustrate the application sequence of a refinement of the concept of linear bellows 25 with consecutively packed folds 25a. In FIG. 4A, within each section of packed folds 25a any initial bellows shrinkage along the Z-direction caused by the suction power from the external electrical air pump 82 is prevented due to mechanical interference. In FIG. 4B, however, a subsequent free expansion of the initially packed folds 25a along the Z-direction into unpacked folds 25b takes place that is driven by the advancing and expanding penis glans 408. Instead of a sectional application, of course, the concept of packed folds 25a can be applied to the structure of the whole elastomeric sleeve 12.

Figure 4C:
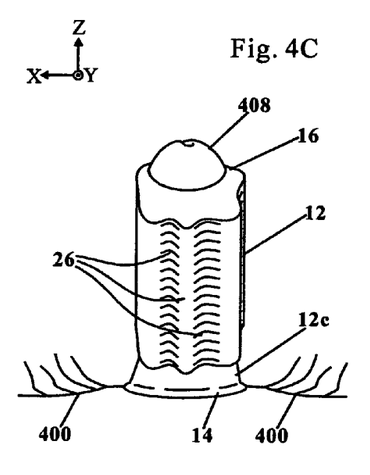
FIG. 4C and FIG. 4D together illustrate the application sequence of another embodiment of angular bellows.
Figure 4D:
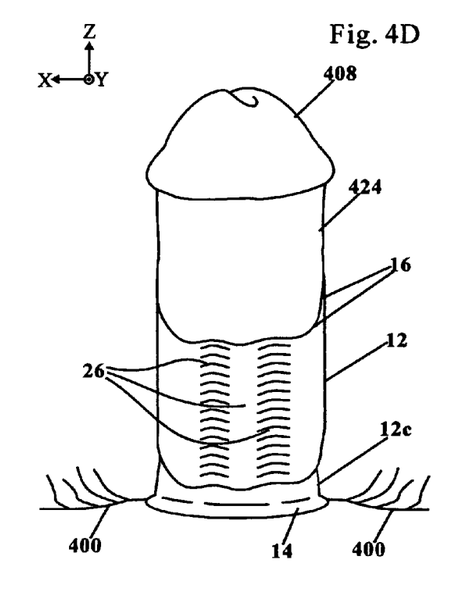

FIG. 4C and FIG. 4D together illustrate the application sequence of another embodiment of angular bellows 26. Here, the angular bellows 26 are expandable along the radial direction making the fully expanded elastomeric sleeve 12 accommodating essentially the entire post-erection penis 424 shaft diameter, FIG. 4D. While not shown here, just like the case of linear bellows the initial geometry of the angular bellows can be made into circumferentially packed folds to prevent an initial radial-direction bellows shrinkage while allowing a subsequent free radial-direction bellows expansion from the advancing and expanding penis shaft during the erection process. By now it should also become clear that the concepts of linear and angular bellows can be combined to form a two-dimensional expandable bellows structure as well.

Figure 5A:
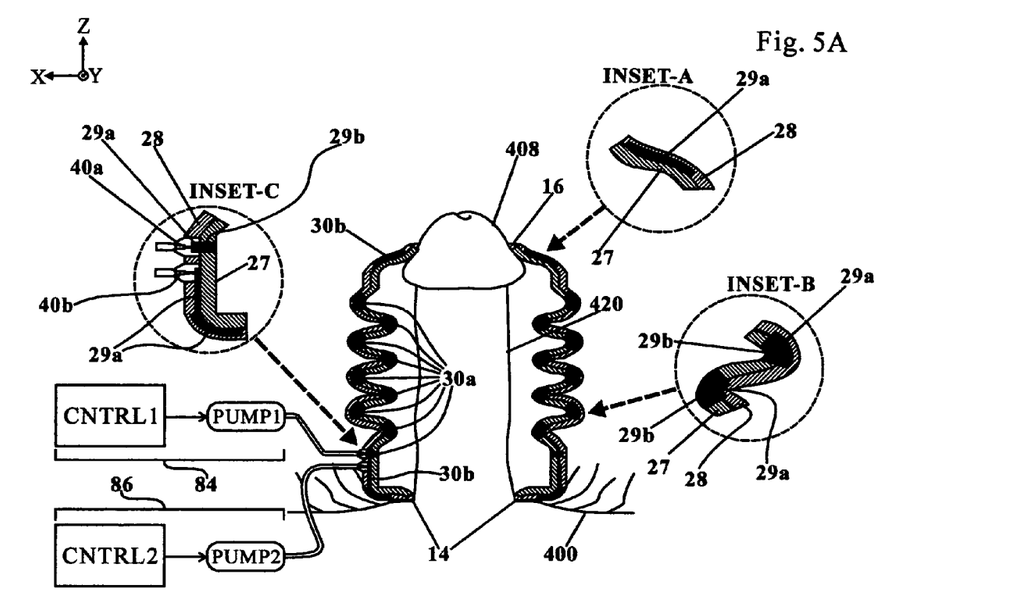
FIG. 5A and FIG. 5B together illustrate the application sequence of another embodiment of a combination of linear bellows plus a two-layer laminate defining two air paths.
Figure 5B:
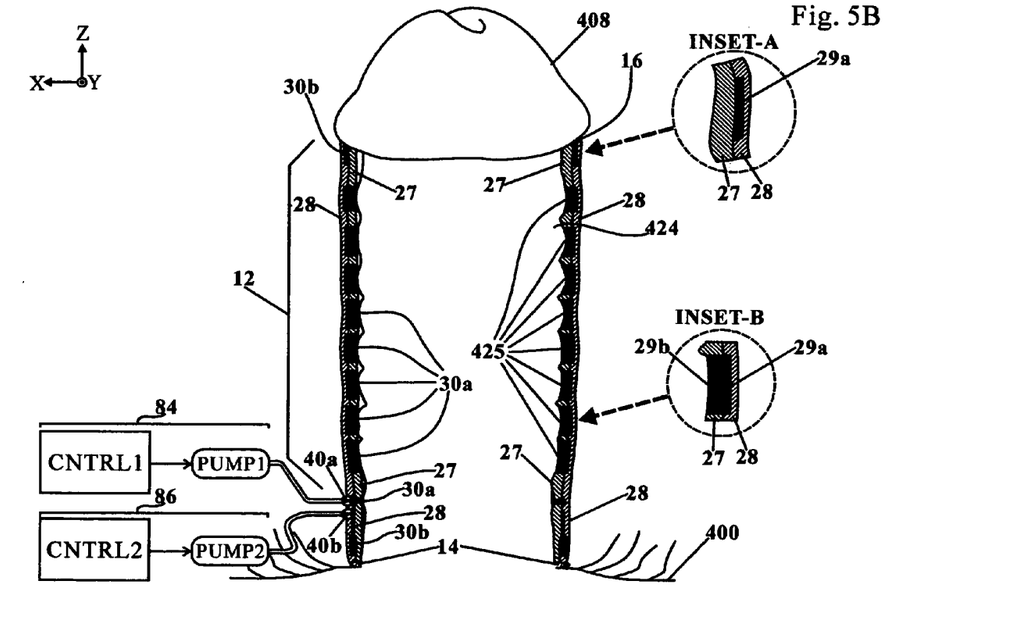

FIG. 5A and FIG. 5B together illustrate the application sequence of another embodiment that is a combination of linear bellows plus a two-layer laminate defining two air paths. Turning now to FIG. 5A with special attention directed to the structural details illustrated in the three insets INSET-A, INSET-B and INSET-C, the wall structure of the elastomeric sleeve 12 is a bellowed laminate of two consecutive layers, layer one 27 and layer two 28. Layer one 27, the layer proximal to the pre-erection penis 420, has a first set of formed through-wall relief patterns 29b routed along its surface. Layer two 28, the layer distal to the pre-erection penis 420, has a second set of formed through-wall relief patterns 29a routed along its surface. The first surface relief pattern set and the second surface relief pattern set jointly define, in this case, two mutually non-communicating air paths air path one 30a and air path two 30b. Air path one 30a freely communicates with the interior of the elastomeric sleeve 12 and air path one 30a is communicatively connected through an externally engageable self-sealing air-port 40a to an electrical air pump one 84 for, in this case, evacuation to a pressure $-\Delta P_1$, below the ambient. On the other hand, air path two 30b is communicatively connected through an externally engageable self-sealing air-port 40b to an electrical air pump two 86 for, in this case, pressurization to a pressure $+\Delta P_2$ above the ambient. Stated another way, the set of air path one 30a and air path two 30b are now controlled, via air-port 40a and air-port 40b, by an external multi-port air pumping device consisting of electrical air pump one 84 and electrical air pump two 86. Hence, following the application sequence from FIG. 5A to FIG. 5B, air path one 30a causes the formation of an expandable and suctioning air tight enclosure of the pre-erection penis 420 resulting in its expansion and erection into the post-erection penis 424 while concomitantly expanding the bellows wall structure of the elastomeric sleeve 12. Meanwhile, air path two 30b causes the pressurization of the aft section 12c near the sleeve base 14 and of the fore section 12a near the front end rim 16 thus hardening and rigidizing them for a better quality coitus. As an illustrative variation, the aft section 12c can instead, through a third air path, be separately evacuated to a pressure $-\Delta P_2$ for restricting blood backflow out of the post-erection penis 424 thus prolonging its erection during and after subsequent coitus.

Figure 5C:
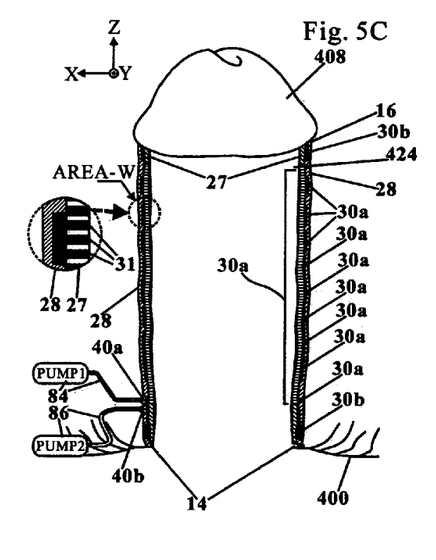
FIG. 5C illustrates another embodiment of the fully expanded erection device with a two-layer laminate defining two air paths and the inner layer proximal to the penis surface having a plurality of through-wall micro pores.
Figure 5D:
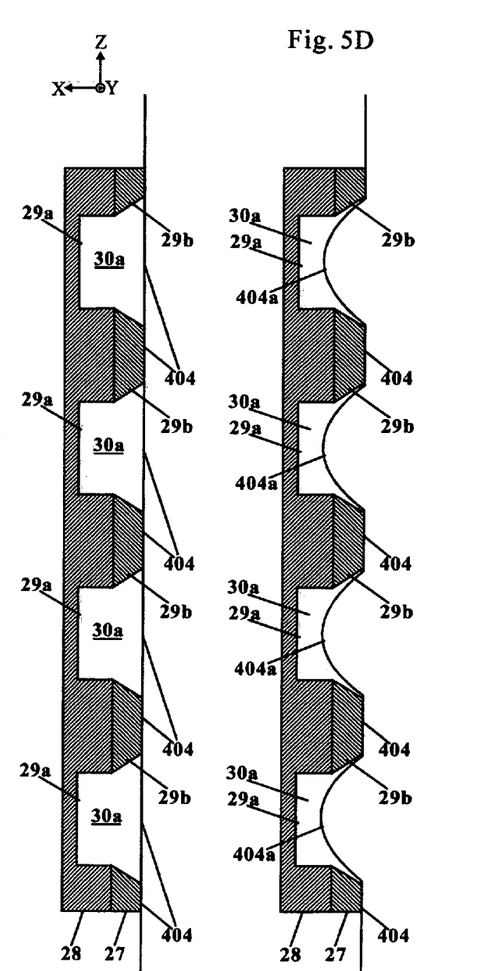
FIG. 5D shows another embodiment illustrated with a surface portion of the fully expanded erection device with a two-layer laminate defining an air path having a plurality of concave scallops.

FIG. 5C illustrates another embodiment of the fully expanded erection device with a two-layer laminate defining two air paths and the inner layer proximal to the penis surface having a plurality of through-wall micro pores. The two layers are layer one 27, the innermost layer proximal to the penis surface, and layer two 28, the outer layer distal to the penis surface. The corresponding air paths are air path one 30a and air path two 30b. With an enlarged detail of AREA-W shown in the inset, the through-wall relief pattern on layer one 27 includes a plurality of through-wall micro pores 31. While the micro pores 31 continue to allow air communication between air path one 30a and the penis surface, the now macroscopically smooth inner surface of layer one 27 prevents the otherwise formation of temporary local nodules 425 (FIG. 5B) on the penis surface while still forming an expandable and suctioning air tight enclosure of the penis. On the other hand, for those users who do not mind the formation of these temporary local nodules 425 on their penis surface this phenomenon can be advantageously used. Thus, FIG. 5D shows another embodiment illustrated with a surface portion of the fully expanded erection device with a two-layer laminate of layers 27 and 28 defining an air path one 30a. As seen on the left side, a plurality of concave scallops, in intimate contact with the penis shaft 404, are formed by the combination of the two-layer laminate, the blind relief patterns 29a on layer two 28 and the through-wall relief patterns 29b on layer one 27. Therefore, on the right side, the formation of an expanded and suctioning air tight enclosure of the penis simultaneously causes, through a negative pressure within the air path one 30a, the build-up of a plurality of matching convex surface scallops 404a from the penis shaft 404. This forms an extra air tight seal against physical movements during subsequent coitus.

Figure 6A:
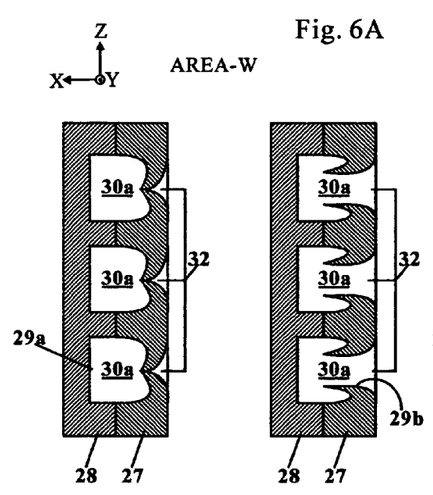
FIG. 6A, FIG. 6B and FIG. 6C illustrate additional variations of the two-layer laminate.
Figure 6B:
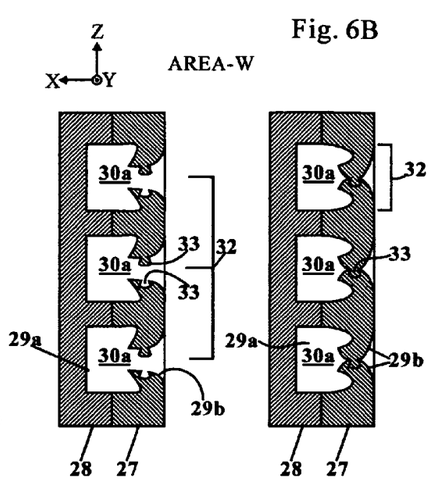
Figure 6C:
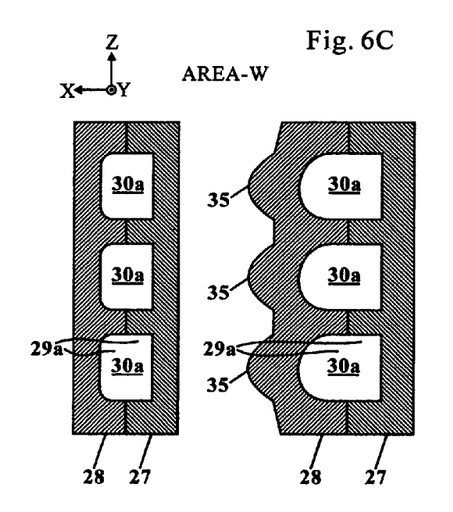
Figure 7A:
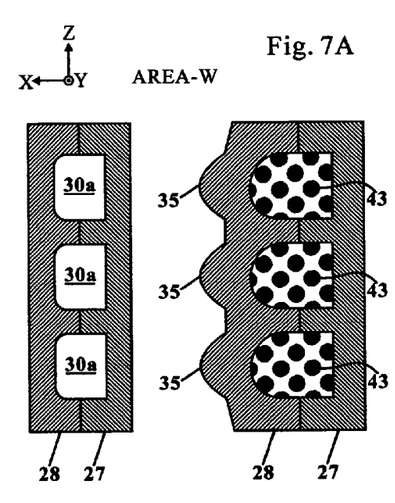
FIG. 7A, FIG. 7B, FIG. 7C and FIG. 7D illustrate more variations of the two-layer laminate exhibiting both static and dynamic erection device surface features.
Figure 7B:
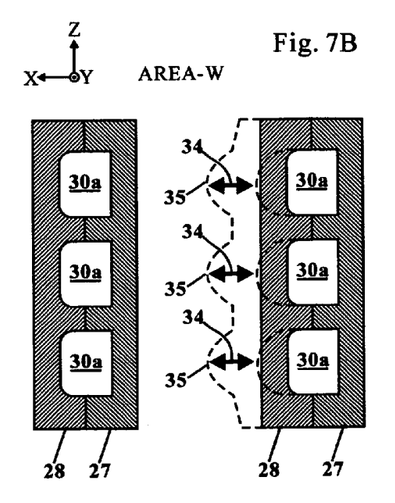
Figure 7C:
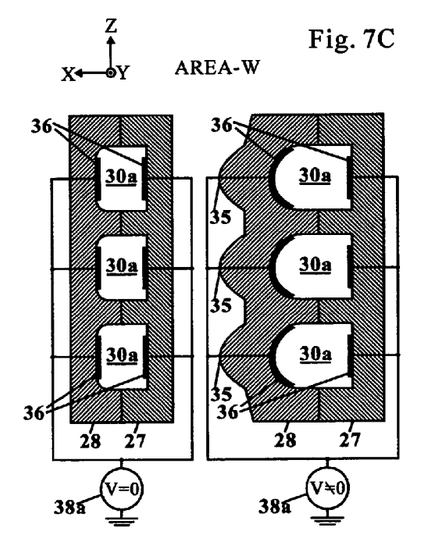
Figure 7D:
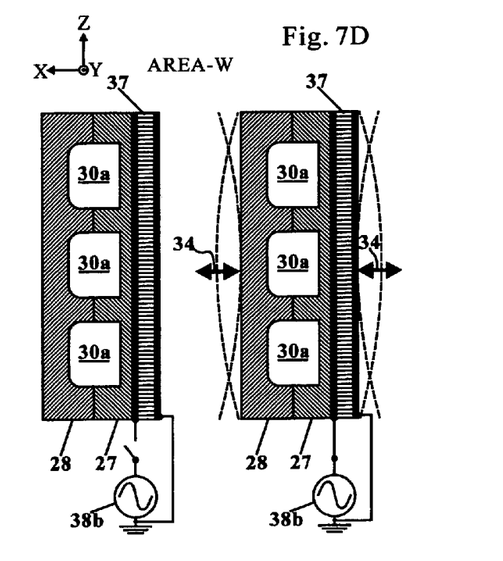

FIG. 6A, FIG. 6B and FIG. 6C illustrate additional variations of the two-layer laminate within the enlarged AREA-W. In the left side of FIG. 6A, the through-wall relief pattern 29b on layer one 27 and the blind relief pattern 29a on layer two 28 are patterned to form a plurality of one-way valves 32 in contact with the penis surface. The plurality of one-way valves 32 function to allow the formation of expandable and suctioning air tight enclosure (right side) of the penis surface while blocking a subsequent loss of suctioning power from air path one 30a during coitus (left side). In the left side of FIG. 6B, the so-formed one-way valves 32 include surface interference features 33 to lock themselves into a closed position (right side) further strengthening their ability to block a subsequent loss of suctioning power from air path one 30a during coitus. The locking action can be effected with a short hand squeeze of the elastomeric sleeve 12 creating a momentary back pressure thus locking the interference features 33 or can be effected with a timed short pressure reversal cycle following the end of the penis erection cycle by programming the electrical air pump one 84. In the left side of FIG. 6C, a portion of the wall of the elastomeric sleeve 12 is made of a high expansion two layer laminate where both layer one 27 and layer two 28 are provided with blind relief patterns 29a forming a number of communicative annular air rings. After engagement with an external multi-port air pumping device and pressurized to a positive pressure relative to the ambient, $+\Delta P$, the significant expansion of these annular air rings correspondingly increase the apparent thickness of the penis shaft 404 while simultaneously creating a number of surface protuberances 35 along the penis surface for subsequent coitus. As a further refinement, these annular air rings can be reconfigured into several mutually non-communicating air path groups with each group engaged to its respective port of the external multi-port air pumping device and sequentially pressurized with a number of sequenced and time varying pressure pulses relative to the ambient thus creating a number of traveling surface protuberances along the Z-axis to further stimulate the penis for subsequent coitus.

FIG. 7A, FIG. 7B, FIG. 7C and FIG. 7D illustrate more variations of the two-layer laminate exhibiting both static and dynamic erection device surface features within the enlarged AREA-W. In the right side of FIG. 7A, after the expanding annular air rings increased the apparent thickness of the penis shaft 404 and simultaneously created the number of surface protuberances 35, the now pressurized air path one 30a can be injected with a soft filling material 43 from an additionally attached filling device hence increasing the hardness of the apparently thickened penis shaft and its surface protuberances. In the right side of FIG. 7B, the above positive pressure relative to the ambient, $+\Delta P$, is made time-varying by programming the multi-port air pumping device thus causing a corresponding surface vibration 34 of the apparently increased thickness and the surface protuberances 35 of the penis shaft. In the left side of FIG. 7C, some members of air path one 30a are lined with a number of opposing electrode pairs 36. The electrode pairs 36 in turn are connected to an electrical signal source 38a. Upon powering by the electrical signal source 38a, the electrical repulsing force established between the electrode pairs 36 causes an increase of the apparent thickness of the penis shaft 404 while simultaneously producing a number of surface protuberances 35 along the penis shaft 404. Of course, the electrical signal source 38a can be made time-varying thus causing a corresponding surface vibration 34 of the apparently increased thickness and the surface protuberances 35 along the penis shaft 404. In the left side of FIG. 7D, an additional piezoelectric layer 37, covered with a number of opposing electrode pairs, is added to the side of the layer one 27-layer two 28 laminate proximal to the penis shaft 404. Upon connection to and powering of the opposing electrode pairs by an external Alternating Current (AC) electrical signal source 38b, the piezoelectric layer 37 can also create a corresponding type of surface vibration 34 along the penis shaft 404 illustrated at the right side of FIG. 7D. Yet another variation is to replace the piezoelectric layer 37 with a resistive heating material to create a corresponding warming of the penis. For safety of the on-genital erection device 10 where electrical power is deployed in the embodiment, as in FIG. 7C and FIG. 7D, any electrical signal or power lines should be embedded within the multi-layer laminate to avoid a direct contact with the penis.

Figure 8:
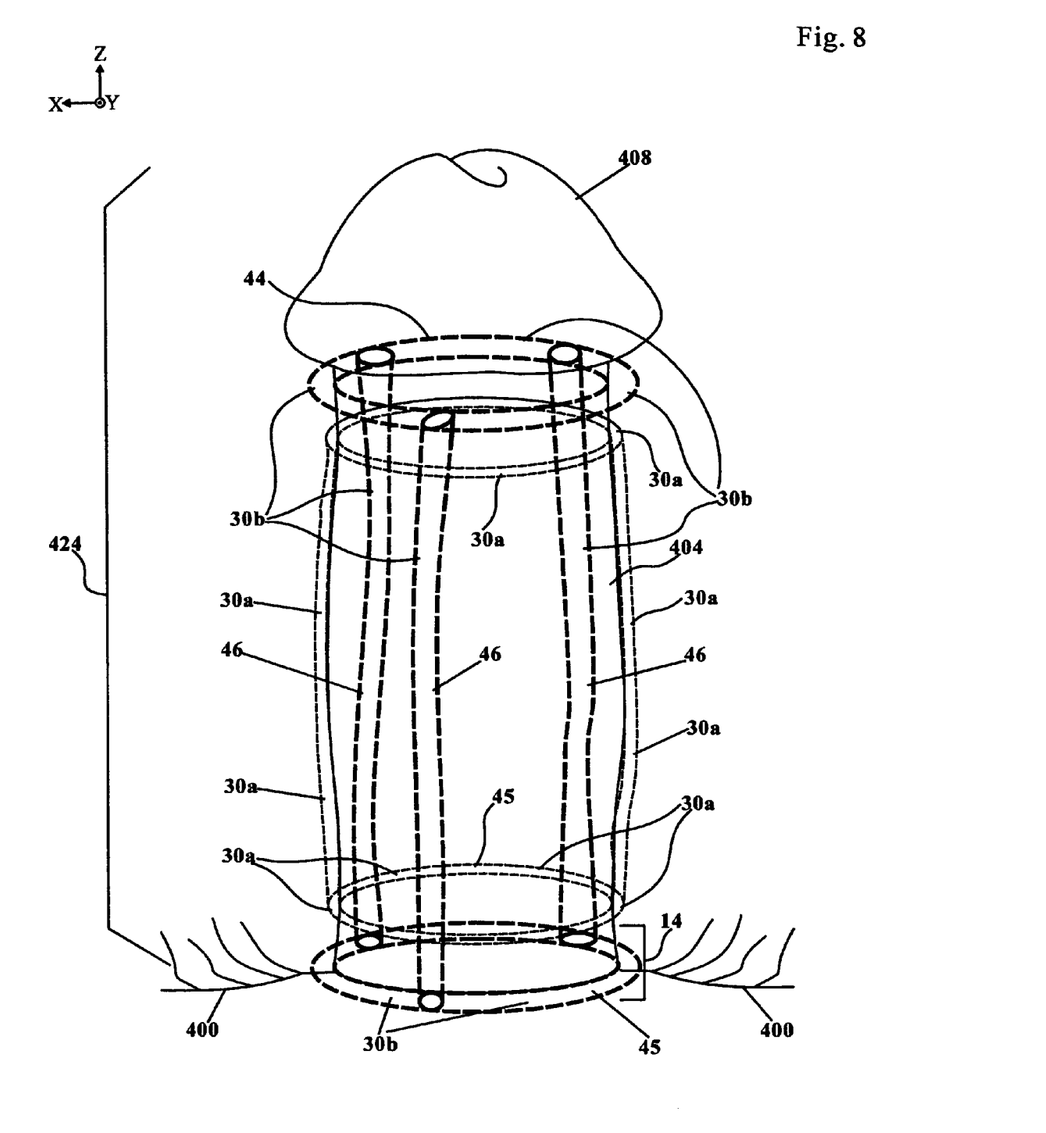
FIG. 8 illustrates only the numerous air paths of the fully expanded erection device of a preferred embodiment with two air paths.

FIG. 8 illustrates only the numerous air paths of the fully expanded on-genital erection device 10 of a preferred embodiment with two air paths. The accompanying multi-layer laminate with numerous blind and through-wall relief patterns are not shown here to avoid unnecessary obscuring details. Like before, the negatively-pressurized air path one 30a has the geometry of an essentially cylindrical sleeve surrounding the bulk of the penis shaft 404. However, the positively-pressurized air path two 30b has the geometry of a strut surrounding the whole penis. The strut is made of the following key elements:

a) An annular base ring 45 surrounding the penis base 400.
b) Three Z-direction columns 46, distributed around the periphery of the penis shaft 404, respectively communicatively connected to the annular base ring 45.
c) An annular glans ring 44, surrounding the penis glans 408, connected to the glans end of the above Z-direction columns 46.

Therefore, the positively-pressurized strut functions to harden and rigidize the whole post-erection penis 424 for subsequent coitus. As a variation, the annular base ring 45 can instead be separated from the strut and negatively-pressurized to form an extra air tight seal against a blood backflow out of the penis hence prolonging the penis erection during and even after subsequent ejaculation.

For those skilled in the art, by now it should become clear that the on-genital erection device can be readily extended to a multi-layer laminate of M layers with N air paths where M>=2 and N>=2. Likewise, by now it should also become clear that the numerous concepts proposed and described here, although for the male genital, can be readily tailored to the female genital as well without departing from the spirit of the present invention. For example, as the tissue and biological structure of the vagina is more or less an inversion of the penis, the fundamental structure of the elastomeric sleeve 12 and its numerous improvements as described here can conceptually be turned inside out and thereafter essentially performing an equivalent function for the vagina.

As described with numerous exemplary embodiments, an easy-to-use on-genital erection device and system for inducing and maintaining the human sexuality are proposed. The on-genital erection device includes a cylindrical elastomeric multi-layer sleeve surrounding the pre-erection penis upon placing the sleeve base at the penis base. The elastomeric sleeve includes through-wall self-sealing air-ports for engaging with an air pumping device thus forming an expandable and suctioning air tight enclosure of the penis surface hence causing its expansion and erection. However, for those skilled in this field, these exemplary embodiments can be easily adapted and modified to suit additional applications without departing from the spirit and scope of this invention. For example, with minor modifications, the on-genital erection device and system is anticipated to be applicable to the female genital as well. Thus, it is to be understood that the scope of the invention is not limited to the disclosed embodiments. On the contrary, it is intended to cover various modifications and similar arrangements based upon the same operating principle. The scope of the claims, therefore, should be accorded the broadest interpretations so as to encompass all such modifications and similar arrangements.

What is claimed is:

1. An on-genital erection device for coital use, the on-genital erection device comprises, under an X-Y-Z Cartesian coordinate system with the direction of an erected penis designated as Z-direction and the penis base plane designated as X-Y plane, a substantially cylindrical elastomeric sleeve surrounding a pre-erection penis upon placement of the sleeve base at a user's penis base, said elastomeric sleeve further comprises at least one through-wall air-ports thereon thereby, after said air-ports get functionally engaged with an external air pumping means, forming an expandable and suctioning air tight enclosure of at least a major portion of the penis surface hence causing a corresponding expansion and erection of the penis for coitus wherein the wall structure of said elastomeric sleeve further comprises a laminate of at least two consecutive layers $L_i$, i=1, 2, . . . , M and M>=2, wherein each $L_i$ further comprises a pre-defined surface relief pattern $RP_i$ thereon such that the corresponding surface relief pattern set $RP_{SET}$, ($RP_1$, $RP_2$ . . . . $RP_M$), jointly define a plurality of air paths $PT_j$ and externally engageable self-sealing air-ports $AP_j$ respectively connected thereto, j=1, 2, . . . , N and N>=2, wherein the plurality of air paths $PT_j$ further comprises a first air path subset $PT_{sub}$ and a second air path subset $PT_k$ and all members of the air path subset $PT_{sub}$ comprising at least one air path $PT_j$ that are adapted to pneumatically communicating with at least a major portion of the penis surface thereby, after said air path subset $PT_{sub}$ get functionally engaged, through said air-ports $AP_j$, with an external multi-port air pumping means, forming an expandable and suctioning air tight enclosure of the penis surface hence causing a corresponding expansion and erection of the penis for coitus.

2. The erection device of claim 1 wherein one or more members of the second air path subset $PT_k$, other than those of the air path subset $PT_{sub}$, are optionally functionally engaged, through a corresponding air-port $AP_k$, with said external multi-port air pumping means and evacuated to a pre-determined negative pressure relative to the ambient, $-\Delta P_k$, thereby adapted to forming an extra air tight seal, in contact with a penis surface area surrounded by said $PT_k$, against physical movements during subsequent coitus.

3. The erection device of claim 2 wherein said one member of the second air path subset $PT_k$ is an annular ring adapted to encircle the penis base thereby forming an extra air tight seal against a back blood flow out of the penis hence prolonging the penis erection during and after subsequent ejaculation.

4. The erection device of claim 1 wherein one or more members of the second air path subset $PT_k$, other than those of the air path subset $PT_{sub}$, are optionally functionally engaged, through a corresponding air-port $AP_k$, with said external multi-port air pumping means and pressurized to a pre-determined positive pressure relative to the ambient, $+\Delta P_k$, thereby adapted to encircle a penis surface area to keep it hard and rigid for subsequent coitus.

5. The erection device of claim 4 wherein said one member of the second air path subset $PT_k$, other than those of the air path subset $PT_{sub}$, is an annular glans ring that is adapted to surround the penis glans thereby facilitates the hardening and rigidizing of the penis glans for subsequent coitus.

6. The erection device of claim 4 wherein said one member of the second air path subset $PT_k$, other than those of the air path subset $PT_{sub}$, is a strut further comprising:
a) an annular base ring adapted to surround the penis base;
b) a plurality of Z-direction columns, distributed around and encircling the periphery of the penis shaft, respectively connected to said annular base ring; and
c) an annular glans ring, adapted to surround the penis glans, connected to the glans end of said Z-direction columns thereby encircling the whole penis hence facilitates the hardening and rigidizing of the whole penis for subsequent coitus.

7. The erection device of claim 1 wherein one or more members of the second air path subset $PT_k$ that are adapted to surround the penis shaft, other than those of the air path subset $PT_{sub}$, are optionally functionally engaged, through a corresponding air-port $AP_k$, with said external multi-port air pumping means and pressurized to a pre-determined positive pressure relative to the ambient, $+\Delta P_k$, thereby adding an artificial thickness to the real thickness of the penis shaft for subsequent coitus.

8. A method of causing an expansion and erection of a user's penis for coitus, the method comprises, under an X-Y-Z Cartesian coordinate system with the direction of an erected penis designated as Z-direction and the penis base plane designated as X-Y plane:

a) surrounding the pre-erection penis with a substantially cylindrical elastomeric sleeve having at least one through-wall air-ports thereon and placing the sleeve base at the penis base;

b) functionally engaging said air-ports with an external air pumping means and forming an expandable and suctioning air tight enclosure of at least a major portion of the penis surface hence causing a corresponding expansion and erection of the penis: and c) providing a laminate of at least two consecutive layers $L_i$, i=1, 2, . . . , M and M>=2 for the wall structure of said elastomeric sleeve, wherein for each $L_i$, further providing a pre-defined surface relief pattern $RP_i$ thereon such that the corresponding surface relief pattern set $RP_{SET}$, ($RP_1$, $RP_2$, . . . , $RP_M$), jointly define a plurality of air paths $PT_j$, further comprising a first air path subset $PT_{sub}$ and a second air path subset $PT_k$, and externally engageable self-sealing air-ports $AP_j$ respectively connected thereto, j=1, 2, . . . , N and N>=2, wherein all members of the air path subset $PT_{sub}$ comprising at least one air path $PT_j$ are together communicatively connected with at least a major portion of the penis surface and functionally engaging said air path subset $PT_{sub}$, through said air-ports $AP_j$, with an external multi-port air pumping means, to form an expandable and suctioning air tight enclosure of the penis surface hence causing a corresponding expansion and erection of the penis for coitus.

9. The method of claim 8 further comprises optionally functionally engaging one or more members of the second air path subset $PT_k$, other than those of the air path subset $PT_{sub}$, through a corresponding air-port $AP_k$, with said external multi-port air pumping means and evacuating said one or more members of the second air path subset $PT_k$ to a pre-determined negative pressure relative to the ambient, $-\Delta P_k$, thereby forming an extra air tight seal at a penis surface area surrounded by said $PT_k$ against physical movements during subsequent coitus.

10. The method of claim 9 further comprises, to form an extra air tight seal against a back blood flow out of the penis hence prolonging the penis erection during and after subsequent ejaculation, making said one member of the second air path subset $PT_k$ an annular ring surrounding the penis base.

11. The method of claim 8 further comprises, to further harden and rigidize the penis, optionally functionally engaging one or more members of the second air path subset $PT_k$, other than those of the air path subset $PT_{sub}$, through a corresponding air-port $AP_k$, with said external multi-port air pumping means and pressurizing said one or more members of the second air path subset $PT_k$ to a pre-determined positive pressure relative to the ambient, $+\Delta P_k$, thereby hardening and rigidizing a penis surface area surrounded by said $PT_k$ for subsequent coitus.

12. The method of claim 8 further comprises, to increase the apparent thickness of the penis shaft for subsequent coitus, optionally functionally engaging one or more members of the second air path subset $PT_k$, other than those of the air path subset $PT_{sub}$, through a corresponding air-port $AP_k$, with said external multi-port air pumping means and pressurizing said one or more members of the second air path subset $PT_k$ to a pre-determined positive pressure relative to the ambient, $+\Delta P_k$, thereby increasing the apparent thickness of the penis shaft.

* * * * *